US008521317B2

(12) United States Patent
Schneider et al.

(10) Patent No.: US 8,521,317 B2
(45) Date of Patent: Aug. 27, 2013

(54) SYSTEMS, METHODS, APPARATUSES, AND COMPUTER-READABLE STORAGE MEDIA FOR DESIGNING AND MANUFACTURING PROSTHETIC DENTAL ITEMS

(75) Inventors: Sascha Schneider, Mühltal (DE); Clemens Groβ, Darmstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 290 days.

(21) Appl. No.: 12/625,410

(22) Filed: Nov. 24, 2009

(65) Prior Publication Data

US 2011/0125304 A1 May 26, 2011

(51) Int. Cl.
*G06F 19/00* (2011.01)

(52) U.S. Cl.
USPC ............................ 700/97; 700/98; 433/177

(58) Field of Classification Search
USPC ..................... 700/97, 98; 433/177
See application file for complete search history.

(56) References Cited

U.S. PATENT DOCUMENTS

| | | | | |
|---|---|---|---|---|
| 4,970,032 A | | 11/1990 | Rotsaert | 264/20 |
| 5,824,111 A | * | 10/1998 | Schall et al. | 623/33 |
| 6,283,753 B1 | * | 9/2001 | Willoughby | 433/172 |
| 6,885,464 B1 | | 4/2005 | Pfeiffer et al. | 356/602 |
| 7,092,784 B1 | * | 8/2006 | Simkins | 700/163 |
| 7,110,844 B2 | * | 9/2006 | Kopelman et al. | 700/118 |
| 7,403,830 B2 | * | 7/2008 | Weber et al. | 700/98 |
| 7,689,308 B2 | | 3/2010 | Holzner et al. | 700/97 |
| 2006/0008776 A1 | | 1/2006 | Orth et al. | 433/215 |
| 2006/0063135 A1 | | 3/2006 | Mehl | 433/223 |
| 2006/0147874 A1 | | 7/2006 | Touchstone | 433/26 |
| 2006/0253215 A1 | * | 11/2006 | Weber et al. | 700/98 |
| 2007/0272120 A1 | | 11/2007 | Engels et al. | 106/35 |
| 2009/0181346 A1 | | 7/2009 | Orth | 433/201.1 |
| 2010/0268363 A1 | * | 10/2010 | Karim et al. | 700/98 |
| 2011/0065065 A1 | * | 3/2011 | Mormann | 433/201.1 |

FOREIGN PATENT DOCUMENTS

| | | |
|---|---|---|
| DE | 199 44 130 A1 | 4/2001 |
| EP | 0 837 659 B1 | 11/1999 |
| EP | 1 859 758 A1 | 11/2007 |
| WO | 02/09612 A1 | 2/2002 |
| WO | 2007/128811 A1 | 11/2007 |

OTHER PUBLICATIONS

"Three-dimensional finite element analysis of stress-distribution around single tooth implants as a function of bony support, prosthesis type, and loading during function", Papavasiliou et al, Journal of Prosthetic Dentistry, Dec. 1996.*

(Continued)

*Primary Examiner* — Michael D Masinick
(74) *Attorney, Agent, or Firm* — Fitzpatrick, Cella, Harper & Scinto

(57) ABSTRACT

A dental CAD/CAM system performs structural analysis of a candidate prosthetic dental item that is to be created using design data representing the prosthetic dental item. The dental CAD/CAM system can recommend positioning of a surface of the prosthetic dental item within a volume of a milling block based on the design data and data representing desired aesthetic properties of the prosthetic dental item. The dental CAD/CAM system can generate and display simulated images of the aesthetic properties of the prosthetic dental item using the design data, data representing the surface of the prosthetic dental item, data representing the volume of the milling block, and data representing aesthetic properties of the milling block. The dental CAD/CAM system can be used to form prosthetic dental items having complex aesthetic properties, such as translucent regions and shades of colors that vary spatially.

24 Claims, 8 Drawing Sheets

(56) References Cited

OTHER PUBLICATIONS

"Numerical Investigations of the Influence of Implant Shape on Stress Distribution in the Jaw Bone", Siegele et al, JOMI on CD-ROM, 1989.*

"Finite element stress analysis on the effect of splinting in fixed partial dentures", Yang et al, Journal of Prosthetic Dentistry, Jun. 1999.*

"Volume Rendering," printed from—www.en.wikipedia.org/wiki/Volume_rendering—6 pages, last modified on May 14, 2010.

Miriah Meyer et al. "Image-Based Volume Rendering with Opacity Light Fields" printed from www.sci.utah.edu/~miriah/research/ibvr,—8 pages.

Herke Jan Noordmans et al., "Spectral Volume Rendering," IEEE Transactions On Visualization and Computer Graphics, vol. 6, No. 3 Jul.-Sep. 2000—12 pages.

* cited by examiner

SYSTEMS, METHODS, APPARATUSES, AND COMPUTER-READABLE STORAGE MEDIA FOR DESIGNING AND MANUFACTURING PROSTHETIC DENTAL ITEMS

BACKGROUND OF THE INVENTION

1. Field of the Invention

The present disclosure relates to computer-aided design and manufacturing, and more particularly to systems, methods, apparatuses, and computer-readable storage media for designing and manufacturing prosthetic dental items, such as teeth or one or more portions thereof.

2. Description of Related Art

Conventionally, a dental restoration procedure that includes creating a prosthetic dental item has been a laborious and time-consuming "trial and error" process. A dentist begins the dental restoration procedure by removing plaque from a patient's teeth in preparation for creating a profile of the patient's teeth and gums. The dentist can create a dental mold of the patient's teeth and gums by capturing a physical impression of the patient's teeth and gums using a molding material. The dental mold is forwarded to a dental laboratory where a physical, three-dimensional model of the patient's teeth and gums is created.

At the dental laboratory, a technician pours plaster into the mold. Once the plaster dries and is removed from the mold, the molded plaster is used as a physical, three-dimensional model of the patient's teeth and gums. If a dental restoration procedure includes replacing a missing tooth with a prosthetic tooth, the technician can build a wax model of the missing tooth using the plaster model of the patient's teeth and gums. The wax model can be used to cast a metal framework to which porcelain will be adhered. The technician adjusts coloring of the porcelain and fires the porcelain and the metal framework in a furnace to bake the porcelain onto the metal framework to create the prosthetic tooth. The technician can add several additional layers of porcelain to the prosthetic tooth to simulate natural color properties (e.g., hue, saturation, and chrominance) of the patient's missing tooth. Once the prosthetic tooth is finished, the technician returns the prosthetic tooth to a dentist, who examines it, and occasionally return it to the laboratory for re-working if problems with the color properties or dimensions of the prosthetic tooth are discovered.

More recently, computer-aided design (CAD) and computer-aided manufacturing (CAM) technologies have been used to create prosthetic dental items. CAD/CAM technologies can be employed to produce prosthetic dental items that fit into a patient's mouth more precisely compared to prosthetic dental items built using conventional techniques. In addition, prosthetic dental items built using CAD/CAM technologies can be produced more quickly than with conventional techniques. For example, Sirona Dental Systems produces a Cerec® system that can be used in a dental professional's office to perform a dental restoration procedure during a single office visit.

When current CAD/CAM technologies are used, a digital representation of a patient's teeth and gums typically is created at the outset of a dental restoration procedure. That is, data representing a three-dimensional surface of a patient's teeth and gums are acquired and stored in a digital data format. There are several advantages to using such digital representations of patients' teeth and gums. For example, immediately after the digital representation of the patient's teeth and gums is created, it can be shared by a dental clinician and a designer of a prosthetic tooth, which can expedite a dental restoration process. In addition, the digital representation of the patient's teeth and gums can be extremely precise.

Aesthetic properties of prosthetic dental items can be extremely important. For example, to make a prosthetic tooth look real or natural in a patient's mouth, color properties of the prosthetic tooth can be matched with color properties of teeth surrounding an area where the prosthetic tooth is to be installed in the patient's mouth. With a conventional manufacturing process, a dental technician akin to an artisan can color and shade the prosthetic tooth using the technician's training, experience, and imagination. An operator of a dental CAD/CAM system may or may not have the same training and experience as a conventional dental technician. Accordingly, it can be useful for a dental CAD/CAM system to assist operators to create prosthetic dental items having aesthetic properties that are comparable or superior to aesthetic properties of dental items created by skilled dental technicians using conventional techniques.

Current dental CAD/CAM systems can employ a ceramic block that is milled by a milling machine to produce a prosthetic dental item. A dentist can select a monochromatic block based upon desired aesthetic properties, e.g., color shading, of the prosthetic dental item to be produced. To determine desired color properties, for example, the dentist can use a template or a computerized shade system, such as the VITA Linearguide 3D-Master® from Vident. Generally, such computerized shade systems do not consider certain aesthetic properties, such as translucency, for example. In addition, a single, monochromatic block cannot always represent certain aesthetic properties of natural teeth, such as complex combinations of hue, saturation, and chrominance of a tooth in a region where the tooth transitions from a gingival surface to an occlusal surface, for example. That is, a single, monochromatic block or polychromatic block often cannot represent gradual transitions in shades of colors that are present in natural teeth.

For example, FIG. 2 shows a simulated image or rendering of a plurality of prosthetic teeth 202-212. Each of the plurality of prosthetic teeth 202-212 includes one or more gradual transitions in shades of colors that can be present in natural teeth.

In addition to having natural aesthetic properties, e.g., coloring, a prosthetic dental item ideally should be mechanically stable to prevent it from breaking prematurely when used by a patient. With conventional manufacturing of prosthetic dental items, a skilled dental technician can produce a prosthetic dental item having a high degree of mechanical stability by applying the dental technician's training and experience. As mentioned, operators of current dental CAD/CAM systems may not always receive the same training as convention dental technicians. In addition, current dental CAD/CAM operators may not have adequate expertise for producing prosthetic dental items having very high degrees of mechanical stability. Accordingly, it is can be useful for a dental CAD/CAM system to assist operators to create prosthetic dental items having mechanical properties that are comparable or superior to mechanical properties of dental items created by skilled dental technicians using conventional techniques.

BRIEF DESCRIPTION OF THE INVENTION

According to an example embodiment herein, a proposed prosthetic dental item can be volume-rendered within a milling block and predicted aesthetic and mechanical properties can be displayed.

According to an example embodiment, shading gradations in a non-monochromatic dental block can be applied to structural property data representing design parameters of a proposed prosthetic dental item and a simulated image of a resulting prosthetic dental item can be displayed.

According to an example embodiment, a model that includes geometric and material properties of a proposed prosthetic dental item can be used to estimate how physically robust the proposed prosthetic dental item will be when manufactured.

According to an example embodiment, a milling block having linear, non-linear, or curvilinear gradations of aesthetic properties can be used to manufacture a proposed prosthetic dental item.

According to an example embodiment, data representing spatially-varying physical and aesthetic properties associated with milling blocks and/or dental items can be used to manufacture a proposed prosthetic dental item.

According to an example embodiment, robustness and an estimated lifetime of a proposed prosthetic dental item can be calculated using models of geometric and material properties of the proposed prosthetic dental item and dentition.

According to an embodiment, modifications to a proposed prosthetic dental item can be suggested.

According to an embodiment, stored data representing a library of mechanical properties of dental materials can be used to calculate structural properties of a proposed prosthetic dental item.

According to an embodiment, stored data representing aesthetic and/or mechanical properties of a milling block, a tooth stump, a prosthetic dental item (including transition zones between the prosthetic dental item and the tooth stump), and teeth surrounding the prosthetic dental item can be used to create the prosthetic dental item.

According to an embodiment, a sub-system of a dental CAD/CAM restorative device can assist an operator to build a prosthetic dental item having natural aesthetic properties and a high degree of mechanical stability.

DETAILED DESCRIPTION

Figure 1A:
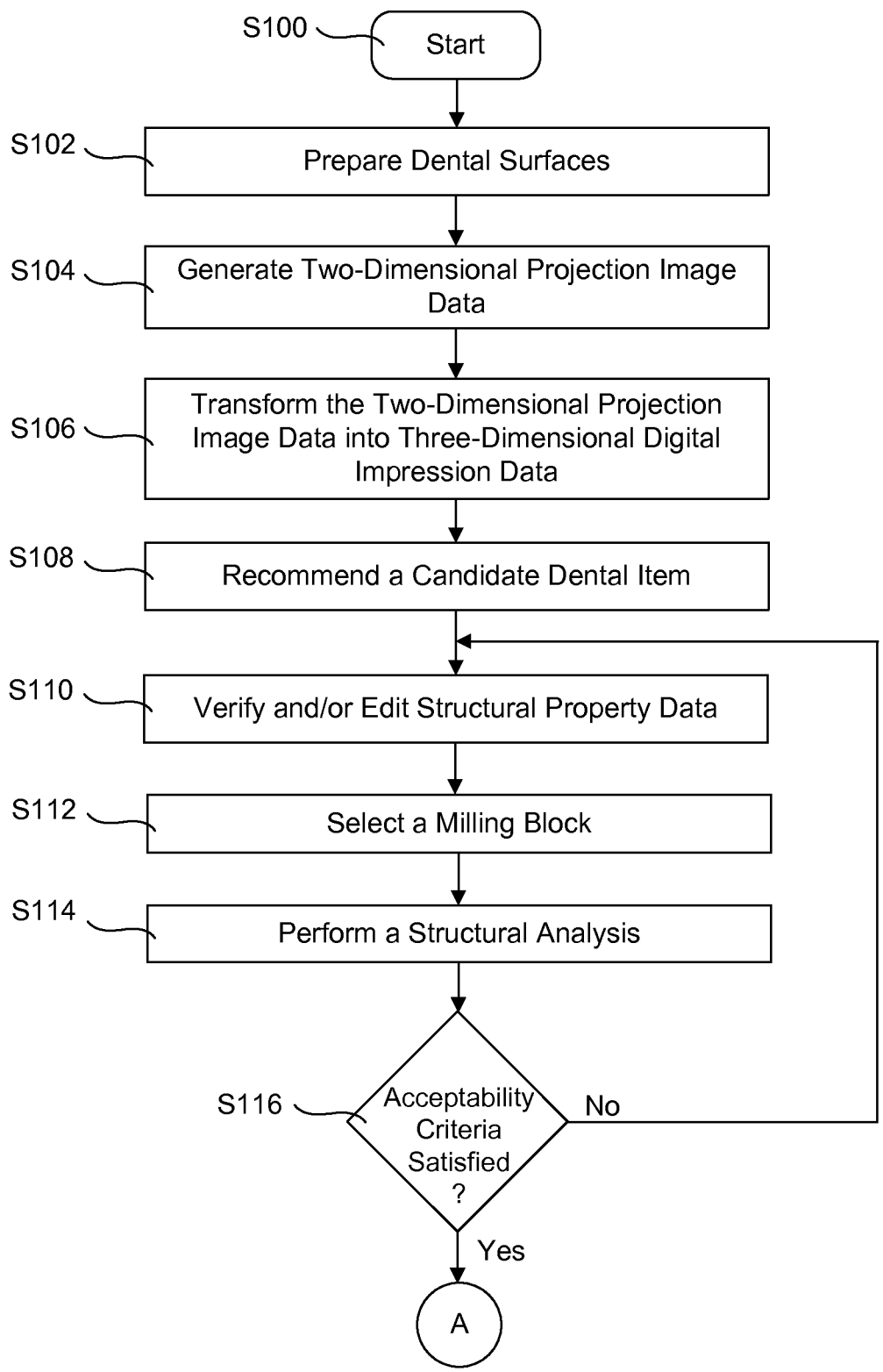
FIGS. 1A and 1B show a flow chart of a process for producing a prosthetic dental item according to an example embodiment herein.
Figure 1B:
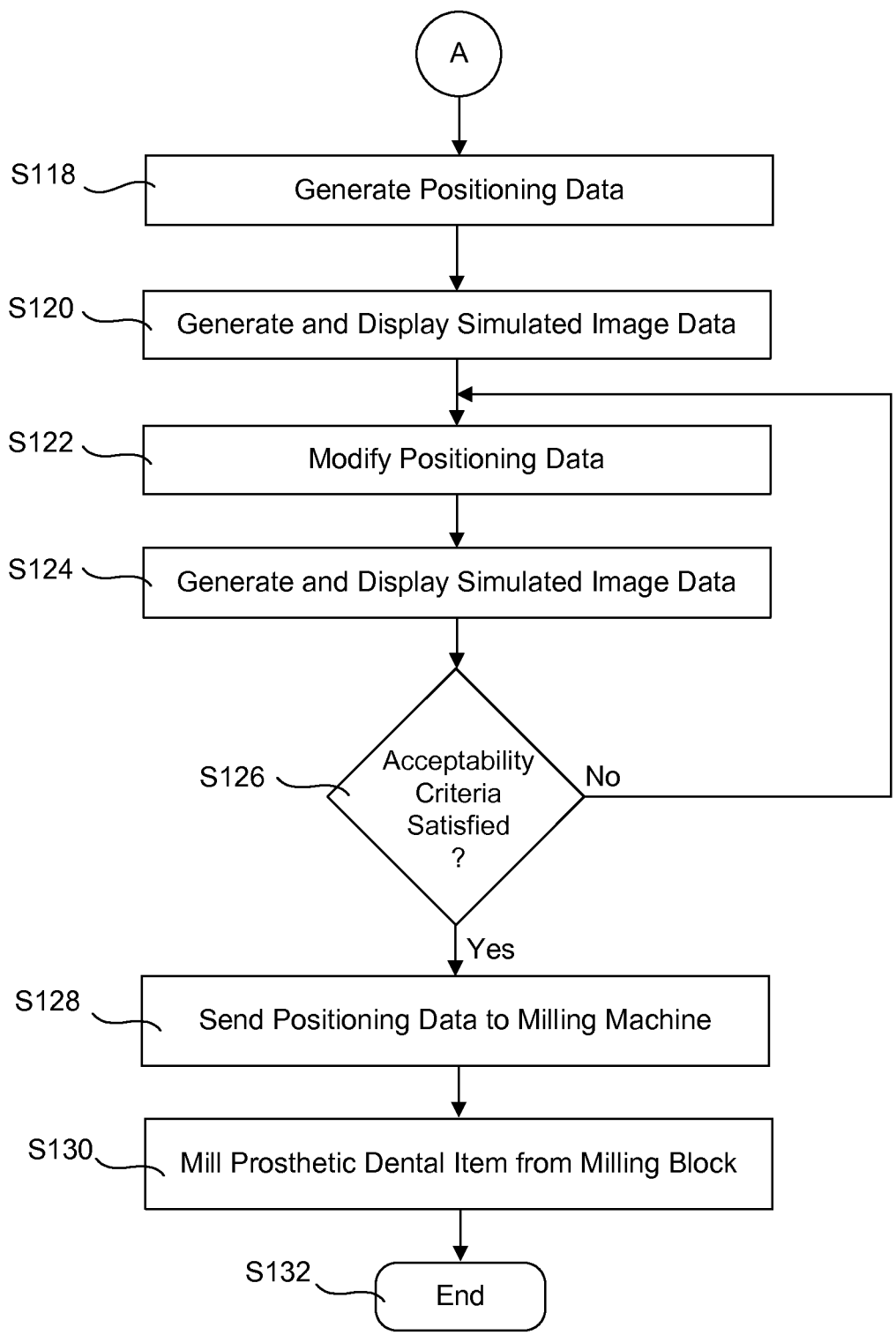

A process of producing a prosthetic dental item according to an example embodiment herein is shown in FIGS. 1A and 1B. The process beings in Step S100. In Step S102, a dentist or a dental hygienist prepares dental surfaces in the mouth of a patient, for example, by removing plaque from dental surfaces of the patient's teeth, which can include, e.g., a tooth stump to which the prosthetic dental item is to be adhered.

In Step S104, data representing a plurality of two-dimensional projection images of the patient's teeth and gums is generated. For example, a camera (e.g., digital camera unit 732) captures multiple images of the patient's teeth and gums and generates image data corresponding to the captured images in a well-known manner. In Step S106, the data representing the two-dimensional projection images are transformed into data representing a three-dimensional digital impression, i.e., digital impression data representing a three-dimensional surface corresponding to the patient's teeth and gums. The data representing the two-dimensional projection images can be generated and transformed into the digital impression data using conventional techniques. For example, U.S. Pat. No. 6,885,464 discloses methods suitable for performing Steps S104 and S106. The contents of U.S. Pat. No. 6,885,464 are incorporated by reference herein in their entirety.

In Step S108, a candidate prosthetic dental item is recommended. For example, stored structural property data that is associated with three-dimensional volume data representing a plurality of prosthetic dental items can be searched to find data representing a candidate prosthetic dental item that will fit into a space where at least one tooth (or one or more portions thereof) once existed based on the digital impression data. The structural property data representing the candidate prosthetic dental item can be retrieved from a library of digital data representing prosthetic dental items that have been designed previously, for example. U.S. Patent Application Publication No. 2006/0063135 discloses one example of an image processing system capable of recommending structural property data representing a candidate prosthetic dental item. The contents of that publication are incorporated by reference herein in their entirety.

In Step S110, structural property data representing design parameters of the recommended prosthetic dental item are verified and/or edited, if deemed necessary. For example, an operator can check a height of a fissure of a tooth stump into which the prosthetic dental item will be placed and change data representing dimensions associated with the prosthetic dental item, if deemed necessary. Similarly, the operator can verify occlusion or adjust contact points and change corresponding structural property data representing design parameters of the prosthetic dental item, if deemed necessary. The structural property data representing the design parameters can be displayed on a computer monitor, for example. If any of the design parameters are to be modified, the operator can change and save structural property data representing modified design parameters using an input device, such as a keyboard or mouse, for example. Data representing the candidate prosthetic dental item can be modified to size and/or orient the prosthetic dental item relative to the patient's teeth and gums using the data representing the candidate prosthetic dental item and the digital impression data.

In one example, these procedures can be performed in a manner such as disclosed in U.S. Patent Application Publication No. 2006/0008776, the contents of which are incorporated by reference herein in their entirety. Other techniques for carrying out Step S110 also can be performed. Software that simulates material properties, e.g., stability, forces during chewing, directions of the forces, torsional moments, can be used to verify the structural property data of the recommended prosthetic dental item. In one example, a material strength in each point of the recommended prosthetic dental item can be evaluated to determine if each point meets a predetermined minimal thickness number. In another example, a physical simulation based on a finite element analysis can be performed using predetermined material properties, which can be stored in a database, and data representing dental surfaces that contact each other in a patient's mouth, which can be obtained by a dental CAD/CAM system.

Data representing a variety of milling blocks each having different aesthetic and/or structural properties can be pre-stored and available for selection. For example, data representing aesthetic properties of a milling bock can include data representing linear, non-linear, and/or curvilinear gradations of shades of colors and/or translucent regions. In Step S112, data representing a particular milling block is selected from among data representing aesthetic and mechanical properties of a plurality of milling blocks. An identifier corresponding to the particular milling block can be selected by an operator using an input device, for example. Alternatively, the identifier corresponding to the particular milling block can be selected by a computer processor (e.g., processor 704) based on pre-stored data representing aesthetic properties of the particular milling block and data representing aesthetic properties of a tooth stump or surrounding teeth. For example, data representing the patient's teeth and gums generated in Step S104 can include color data representing one or more colors of the patient's teeth and gums and the data representing the particular milling block can include color data representing one or more colors of the milling block. A processor can select the particular milling block by determining that the color data of the particular milling block are more highly correlated with color data of the patient's teeth and gums than color data of other milling blocks.

Before describing Step S114 in detail, it is noted that data representing the candidate prosthetic dental item and the selected milling block can be used to predict aesthetic and structural (mechanical) properties (see Steps S114 and S124, respectively, below) of a resulting prosthetic dental item that is formed from the selected milling block based on structural property data representing the design parameters of the candidate prosthetic dental item. For example, pre-stored data representing the candidate prosthetic dental item can be retrieved from a database in Step S108, which data can be modified in Step S110, if deemed necessary. As mentioned, the aesthetic and mechanical properties of the resulting prosthetic dental item may vary spatially. For example, the resulting prosthetic dental item can be designed to have translucent portions and gradual transitions of shades of colors that vary spatially.

Once the structural property data representing design parameters of the candidate prosthetic dental item have been verified (and edited, if deemed necessary) (Step S110) and the milling block has been selected (Step S112), then in Step S114, a structural (mechanical) analysis of the resulting prosthetic dental item, tooth stump, and/or surrounding teeth is performed based on pre-stored data representing structural properties of the prosthetic dental item, tooth stump, and/or surrounding teeth. For example, a stress distribution of at least one tooth stump to which the prosthetic dental item is to be attached can be calculated. Similarly, a stress distribution of the prosthetic dental item and a stress distribution of teeth surrounding the prosthetic dental item can be calculated by simulating forces generated during chewing, directions of these forces, and torsional moments. Techniques for calculating stress distributions, which can include solving partial differential equations, are known in the art. For example, finite element analysis, computational fluid analysis, and rigid beam analysis techniques can be used. Using one or more of these techniques, one or more locations of structural weaknesses, if any, can be identified by a computer system. A patient's bite and corresponding biting forces can be simulated. Physical properties of materials having at least one surface opposite a surface of the prosthetic dental item can be included in the structural analysis. Such materials can include natural tooth enamel, amalgam, gold, and/or other prosthetic dental items, such as those formed from ceramic materials, for example.

In Step S116, a determination is made as to whether the candidate prosthetic dental item satisfies specified acceptability criteria. For example, a stress distribution calculated in Step S114 can be compared to a nominal stress distribution in Step S116. In one example, if the calculated stress distribution is less than the nominal stress distribution, the candidate prosthetic dental item can be determined to satisfy the acceptability criteria. If one or more of the acceptability criteria are not satisfied (e.g., the stress distribution is equal to or greater than the nominal stress distribution), Step S110 through Step S116 can be repeated until a particular combination of candidate prosthetic dental item and milling block is determined to satisfy the acceptability criteria.

If the acceptability criteria (e.g., structural design requirements) are satisfied, position data representing a three-dimensional volume of the prosthetic dental item within a three-dimensional volume of the milling block is generated and recommended to an operator in Step S118. For example, a computer system calculates a preferred location, degree of rotation, and/or orientation of the three-dimensional volume of the prosthetic dental item within the three-dimensional volume of the milling block using algorithms for shape correlation and minimization of shape errors. The preferred location, degree of rotation, and/or orientation can be recommended to an operator who accepts or modifies these parameters. To determine whether the acceptability criteria are satisfied, a minimization algorithm that matches a shape of a constructed restoration to a color gradient field of a block that meets certain predetermined conditions can be used. For example, a predetermined condition can require that occlusion is located towards a brighter side of a material. The minimization algorithm can be realized using a matrix equation for vertex coordinates of mesh points and a color-field of the block.

Data representing a simulated image or three-dimensional rendering of a resulting prosthetic dental item (i.e., a prosthetic dental item formed from the selected milling block based on the positioning data generated in Step S118) can be generated and displayed on a computer monitor in Step S120. In Step S122, the operator can modify, based on the displayed image or rendering, data representing positioning of the volume of the prosthetic dental item within the volume of the selected milling block to change aesthetic properties of the prosthetic dental item. For example, the operator can change data representing a location, degree of rotation, and/or an orientation of the volume of the prosthetic dental item within the volume of the milling block using a mouse (two-dimensional or six-dimensional) or cursor keys. In one example embodiment, the procedure can prevent the operator from positioning the volume of the prosthetic dental item outside the volume of the milling bock.

In Step S124, data representing a simulated image showing aesthetic properties of the prosthetic dental item when installed in the patient's mouth can be generated and displayed and/or rendered on a display unit of a dental CAD/CAM system. Volume rendering techniques can be employed to generate the simulated image showing the aesthetic properties of the prosthetic dental item. Example volume rendering techniques are described in a document entitled "Volume Rendering," which is available at http://en.wikipedia.org/wiki/Volume_rendering (last accessed Oct. 14, 2009). In one example, a gray density visualization can be used, in which one dimensional information (e.g., a grayscale value) is provided for each point of data representing a three-dimensional volume of the prosthetic dental item. In one example, a color density visualization can be used, in which three-dimensional information (e.g., a red component value, a green component value, and a blue component value) is provided for each point of data representing the three-dimensional volume of the prosthetic dental item.

Data representing a three-dimensional volume of the prosthetic dental item can be used to generate the simulated image of the prosthetic dental item installed in the patient's mouth. A database storing a library of digital data representing prosthetic dental items that have been designed previously can provide, for example in Step S108, the data representing the three-dimensional volume of the prosthetic dental item. For example, data representing the aesthetic properties of the prosthetic dental item can be generated based on data representing positioning of the prosthetic dental item in the patient's mouth, demographic data, data representing aesthetic properties of a tooth stump to which the prosthetic dental item will be attached, and/or data representing aesthetic properties of surrounding teeth. As an example, the aesthetic properties of the surrounding teeth can be acquired using techniques disclosed in European Patent No. 0 837 659, the contents of which are incorporated by reference herein in their entirety.

Figure 2:
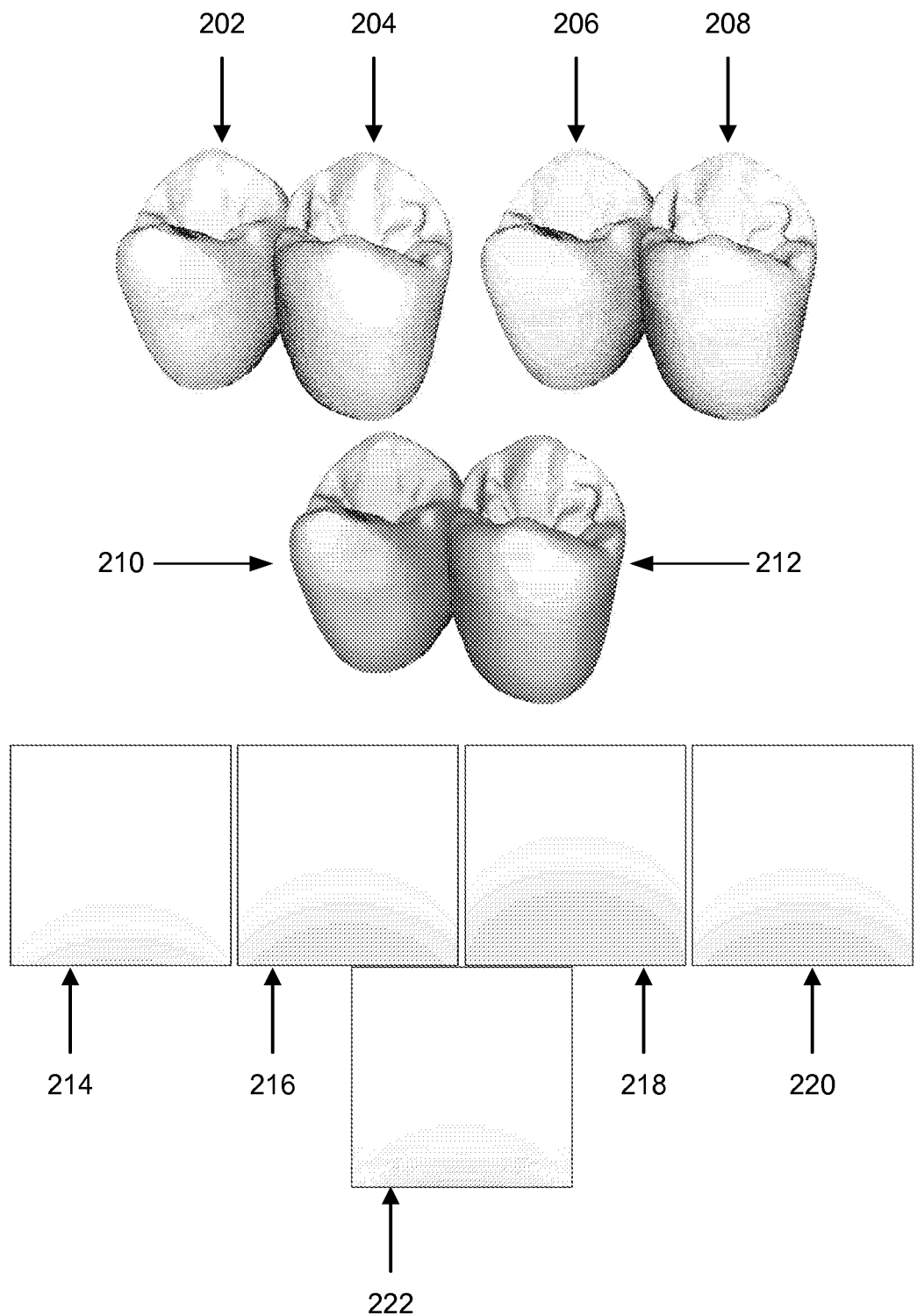
FIG. 2 shows a simulated image of prosthetic dental items having gradual transitions in coloring and shading properties according to an example embodiment.

The data representing the simulated image in Step S124 includes data representing the aesthetic properties of the prosthetic dental item and can be generated based on the data representing the volume of the prosthetic dental item, the data representing the volume of the milling block, and associated data representing aesthetic properties of the milling block. In one example, data representing aesthetic properties can be generated based on simulated lighting conditions and viewing angles using known techniques, such as ray tracing techniques and ray casting techniques. When a ray casting technique is used, for every pixel to be displayed on a computer screen, simulated light is projected through the volume of the prosthetic dental item and effects of reflection, absorption, refraction, and shadowing are computed. Using another technique, the volume of the prosthetic dental item can divided into slices of predetermined thicknesses, which are rendered on top of one another. FIG. 2 shows rectangular slices 214-222 of a milling block that can be used to display or render a prosthetic tooth 210, for example. Such a technique can be employed using a relatively basic video graphics card. Volume rendering algorithms also can be used. For example, the publications by Meyer et al., entitled "Image-Based Volume Rendering with Opacity Light Fields" (available at http://www.sci.utah.edu/~miriah/research/ibvr, last accessed Sep. 25, 2009) and by Noordmans et al., entitled "Spectral Volume Rendering," IEEE Transactions on Visualization and Computer Graphics, vol. 6, no. 3, pp. 196-207, July-September 2000, both of which are incorporated by reference herein in their entirety, describe examples of suitable volume rendering algorithms that can be employed. Volume rendering algorithms can be computationally intensive.

In Step S126, an indication of whether one or more acceptability criteria (e.g., aesthetic properties of the prosthetic dental item) are satisfied is received. For example, simulated aesthetic properties of the prosthetic dental item can be displayed on a computer monitor and an operator can indicate whether the simulated aesthetic properties are acceptable using an input device, such as a keyboard or a mouse, for example. Alternatively, acceptability can be determined automatically based on predetermined acceptability criteria. As an example, data representing aesthetic properties of the patient's teeth and gums and data representing aesthetic properties of the prosthetic dental item can be correlated to determine whether the acceptability criteria have been satisfied.

If one or more of the acceptability criteria of the prosthetic dental item are determined not to be satisfied, Step S122 through Step S126 can be repeated until a particular positioning of the volume of the prosthetic dental item within the volume of the milling block is determined to satisfy the acceptability criteria. For example, to modify data representing positioning of the volume of the prosthetic dental item within the volume of the selected milling block in Step S122, an operator can use an input device to rotate and/or translate a displayed volume of the prosthetic dental item within a displayed volume of the selected milling block. When a dental restoration process is performed by a dental CAD/CAM system, multiple views can be supported and an operator can use radio buttons, for example, to select and unselect various features (e.g., a tooth stump or a surrounding tooth) for displaying on a display unit of the dental CAD/CAM system.

If the acceptability criteria associated with the prosthetic dental item are determined to be satisfied in Step S126, the selected milling block and data representing positioning of the volume of the prosthetic dental item within the volume of the selected milling block (e.g., automatically generated in Step S122 as a result of the operator positioning of a displayed volume of the prosthetic dental item within a displayed volume of the selected milling block) are stored in a computer memory unit and/or sent to a destination in Step S128. For example, a file including the data representing the positioning of the volume of the prosthetic dental item within the volume of the selected milling block, and the selected milling block, can be transmitted over a network to another computer (such as, e.g., a computer of a milling machine or otherwise), and/or data representing the selected milling block can be emailed to an email address where the milling machine is located. Alternatively, the data representing the positioning of the volume of the prosthetic dental item within the volume of the selected milling block, and the selected milling block, can be transmitted over a communications bus to a sub-system (such as, e.g., computerized milling unit 734) performing milling functions and the selected milling block can be delivered to the sub-system performing milling functions using a mechanized sub-system, such as one or more conveyor belts and robotic arms, for example.

In Step S130, the milling machine can use the data representing the positioning of the volume of the prosthetic dental item within the volume of the milling block to control a cutting arm that mills the milling bock to form the prosthetic dental item having structural properties (e.g., dimensions, etc.) specified in Step S110 and aesthetic properties (e.g., gradual transitions of shades of colors) simulated in Step S120 and/or Step S124. The process ends in Step S132.

Figure 3:
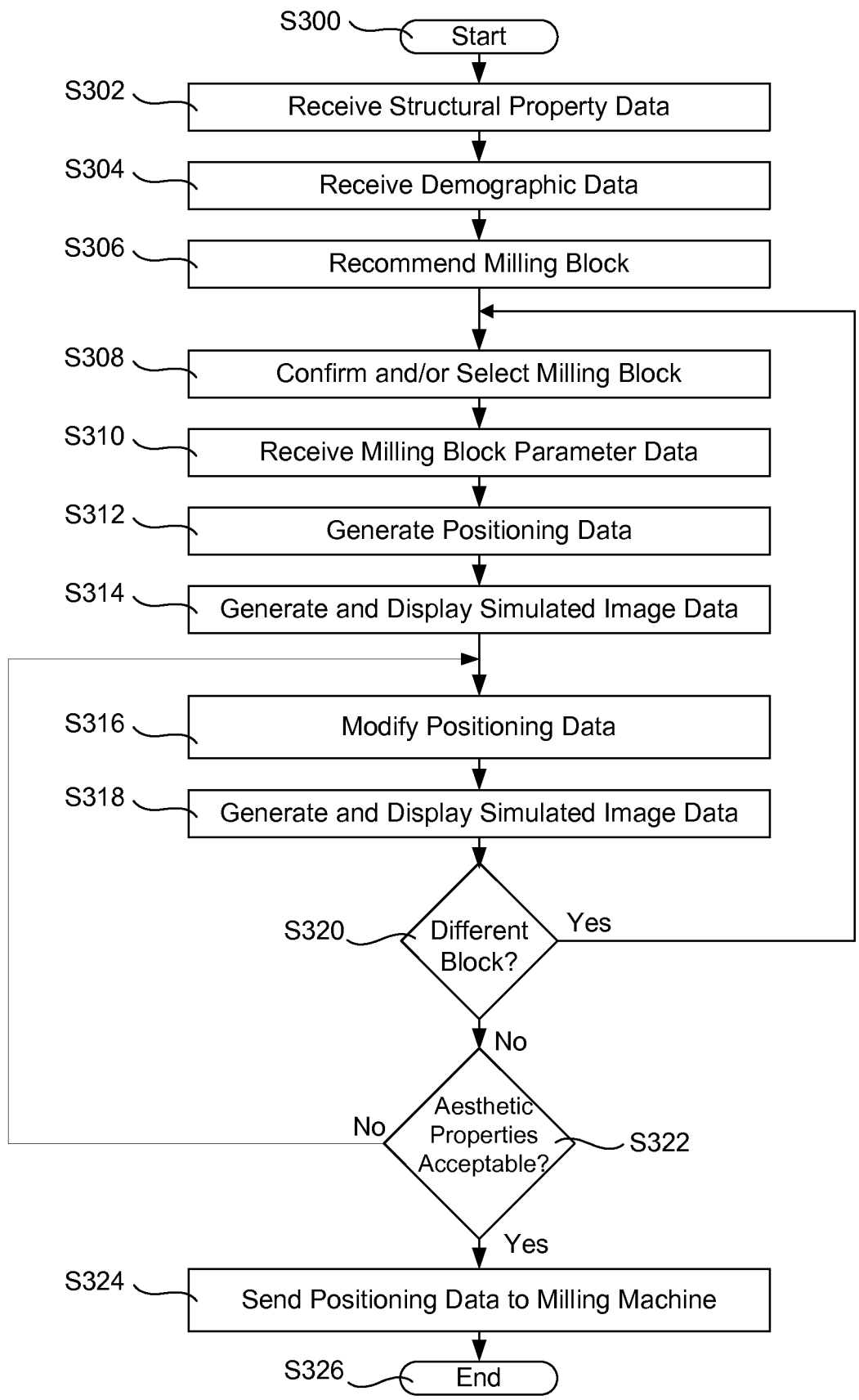
FIG. 3 shows an iterative process according to an example embodiment.

FIG. 3 shows an iterative process for designing a prosthetic dental item according to an example embodiment. The process begins in Step S300. In Step S302, structural property data representing design parameters are received. For example, an operator of a dental CAD/CAM system that is constructed and operated according to this embodiment uses an input device to enter a size and/or dimension of the prosthetic dental item to be produced. Additionally, using the input device the operator can specify occlusion and/or contact points of the prosthetic dental item. In Step S304, demographic data is received. For example, an operator can input a tooth number corresponding to a tooth to which the prosthetic dental item to be created (e.g., a cap, crown, or bridge) will be attached.

In Step S306, a particular milling block is recommend based on the data received in Steps S302 and S304. If the operator is satisfied with the recommended milling block, the operator can confirm the recommended milling block in Step S308. The operator also can select an alternative milling block from a list of available milling blocks, for example, in Step S308.

Figure 4:
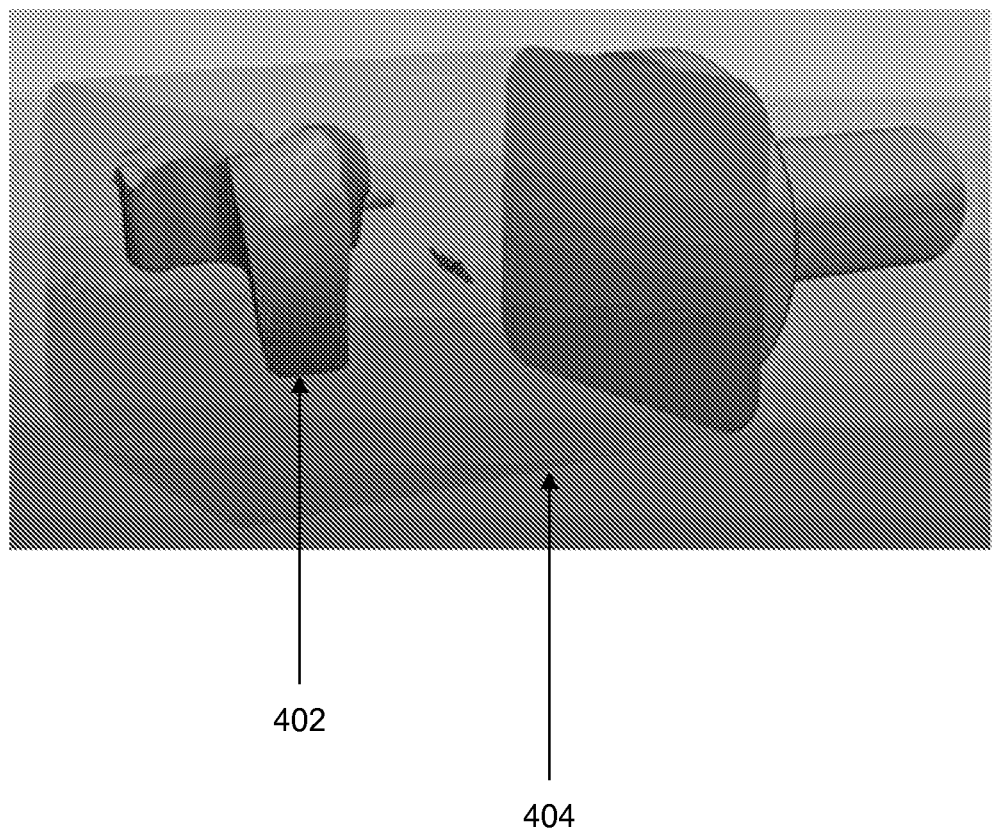
FIG. 4 shows a simulated image of a three-dimensional volume of a prosthetic dental item within a three-dimensional volume of a milling block according to an example embodiment.

In Step S310, data representing one or more parameters of the selected milling block are received. For example, data representing one or more values of tensile strengths of a ceramic material from which the selected milling block is formed and/or other types of values relating to structural and/or aesthetic characteristics of the milling block can be retrieved from a database. In Step S312, data representing positioning of the volume of the prosthetic dental item within the volume of the milling block is generated and recommended to an operator based, at least in part, on the design parameter data received in Steps S302, the demographic data received in Step S304, and the milling block parameter data received in Step S310. In Step S314, the dental CAD/CAM system generates and displays data representing a simulated image of the prosthetic dental item within the milling block using the positioning data generated in Step S312. For example, in Step S314, the dental CAD/CAM system can display a volume of a prosthetic dental item 402 within a volume of a milling block 404, as shown in FIG. 4.

If the prosthetic dental item is to be milled from the milling block using current positioning data representing the volume of the prosthetic dental item within the volume of the milling block, a resulting prosthetic dental item will have particular aesthetic properties. To determine whether these aesthetic properties are acceptable, data representing a simulated image of a three-dimensional overlay of the resulting prosthetic dental item can be generated and displayed in Step S314. The data representing the simulated image of the three-dimensional overlay can include data representing the milling block, the resulting prosthetic dental item, a tooth stump to which the prosthetic dental item will be attached and/or surrounding teeth, for example.

Figure 5:
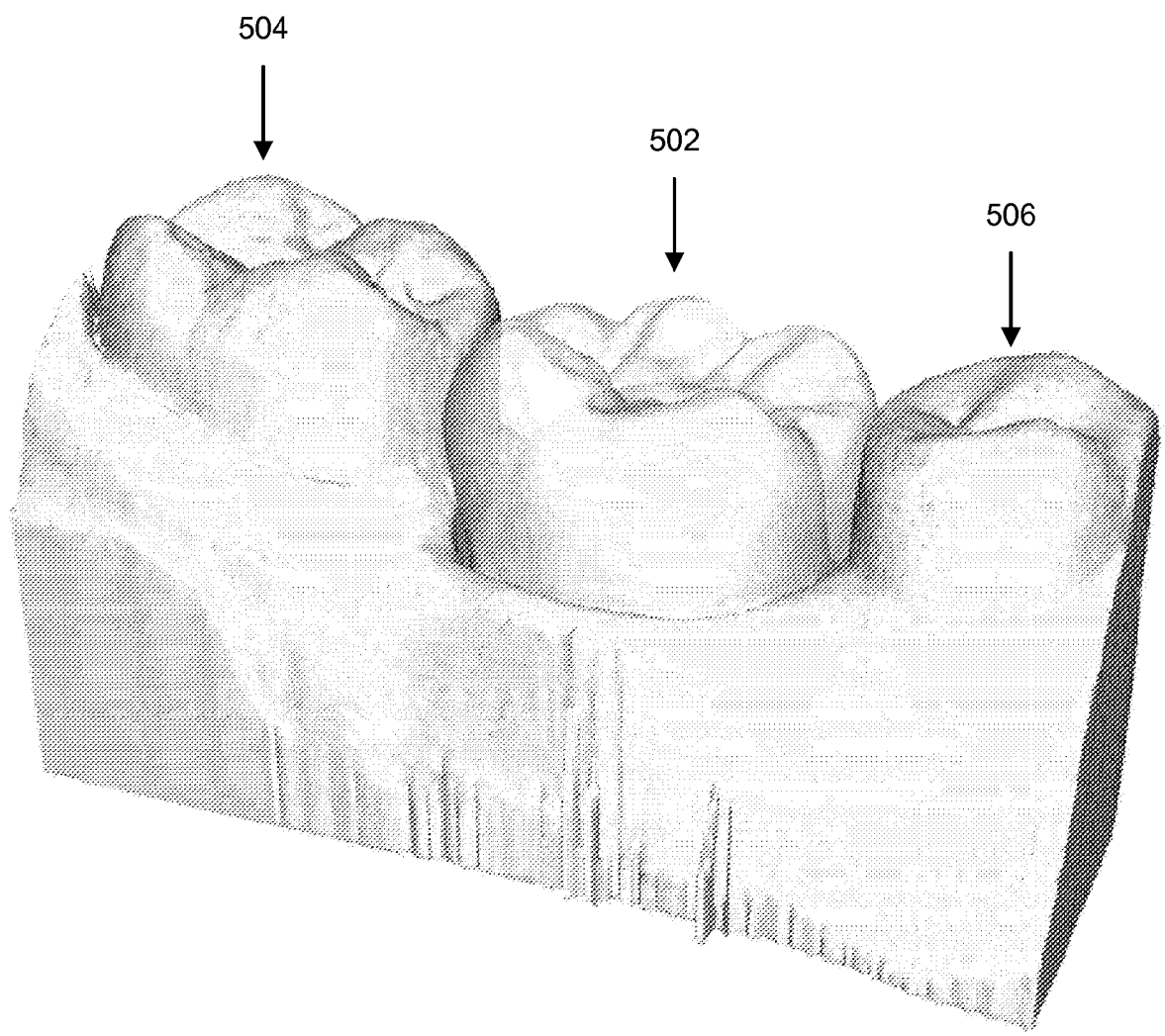
FIG. 5 shows a simulated image of a prosthetic tooth installed in a patient's mouth according to an example embodiment.
Figure 6:
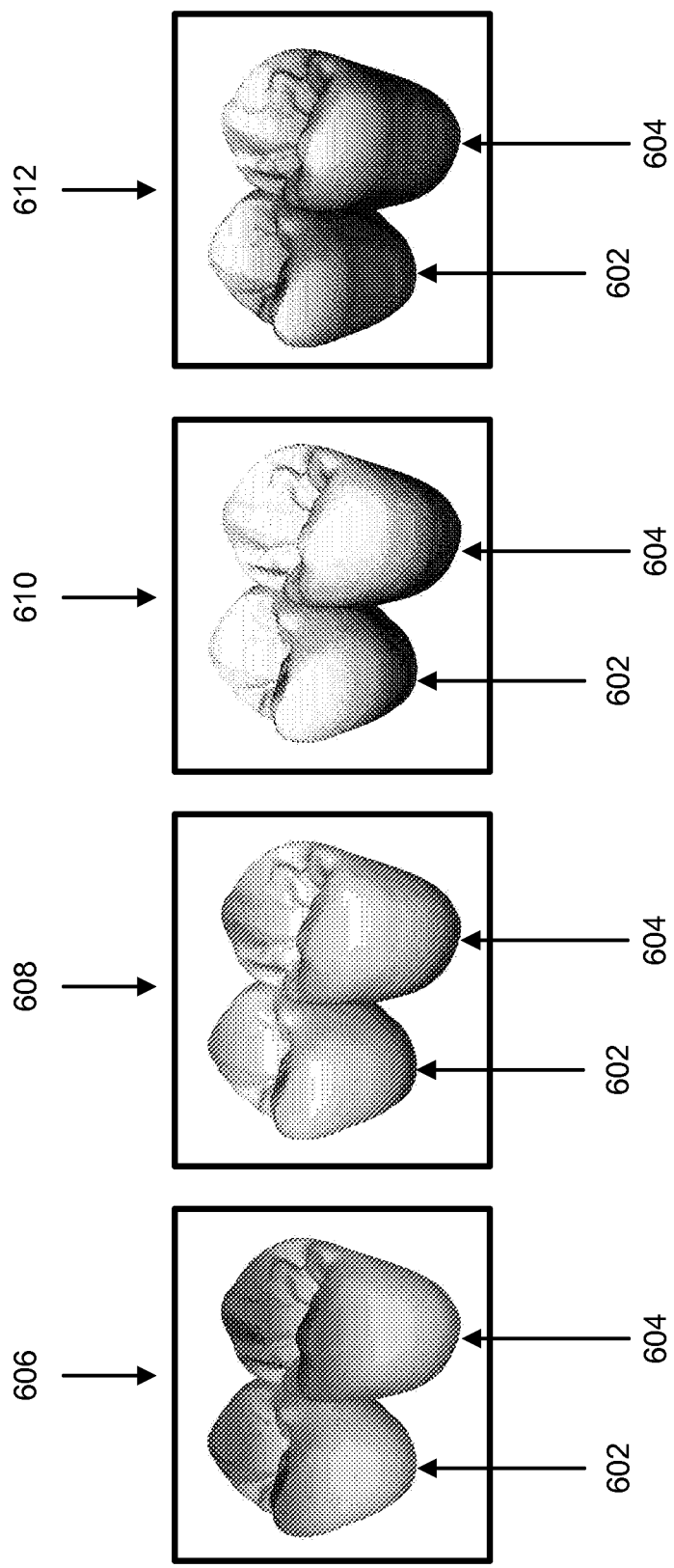
FIG. 6 shows a simulated image of a prosthetic tooth and surrounding teeth structures according to an example embodiment.

In addition, the dental CAD/CAM system can generate and display data representing a simulated image of a three-dimensional overlay that includes data representing a prosthetic tooth 502 installed in a patient's mouth between surrounding teeth 504 and 506, for example, as shown in FIG. 5. The dental CAD/CAM system also can generate (with or without operator input) and display (with or without operator input) data representing simulated images 606-612, each of which can correspond to a different simulated lighting condition, for example, as shown in FIG. 6. In one example, the lighting conditions can be determined by boundary conditions of light simulated during volume rendering of a scene. For example, lighting conditions can be determined using a light source that illuminates teeth (from behind the teeth or from the front of the teeth). Of course, these procedures also can be performed automatically, with or without operator input.

Display data representing a simulated image or three-dimensional rendering of the resulting prosthetic dental item can be generated and displayed on a computer monitor in Step S314. In Step S316, the operator can modify positioning data representing the volume of the prosthetic dental item within the volume of the selected milling block to change aesthetic properties of the prosthetic dental item in a manner similar to that described above in reference to Step S122.

In Step S318, data representing one or more simulated images including data representing aesthetic properties of the prosthetic dental item can be generated and displayed or rendered on a display unit of a dental CAD/CAM system. In Step S320, an indication of whether a different milling block is to be selected is received. For example, an operator of the dental CAD/CAM system can indicate whether a different milling block is required using an input device, such as a keyboard or a mouse. If an indication that a different milling block is to be selected is received in Step S320, Step S308 through Step S318 can be repeated until a different milling block is no longer needed.

On the other hand, if an indication that a different milling block is not to be selected is received in Step S320, an indication of whether the simulated aesthetic properties of the prosthetic dental item are acceptable is received in Step S322. For example, aesthetic properties of the prosthetic dental item can be displayed on the display unit and the operator can indicate whether the simulated aesthetic properties are acceptable using an input device, such as a keyboard or a mouse, for example. Alternatively, acceptability can be determined automatically based on predetermined acceptability criteria.

In Step S322, if the simulated aesthetic properties of the prosthetic dental item are determined not to be acceptable, Step S316 through Step S320 can be repeated until a particular positioning of the volume of the prosthetic dental item within the volume of a particular milling block is determined to produce acceptable, simulated aesthetic properties. If the simulated aesthetic properties of the prosthetic dental item are determined to be acceptable in Step S322, then in Step S324 the selected milling block and data representing the positioning of the volume of the prosthetic dental item within the volume of the selected milling block can be outputted and/or milled as described above with respect to Steps S128 and S130.

The process ends in Step S326. In one example embodiment, the milling machine can use the data representing the volume of the prosthetic dental item within the volume of the milling block to control a cutting arm of the milling machine to mill the milling bock to form the prosthetic dental item in Step S326 having structural properties (e.g., dimensions, etc.) specified in Step S302 and aesthetic properties (e.g., gradual transitions of shades of colors) simulated in Steps S318 and/or S314.

Example aspects described herein may be implemented using hardware, software, or a combination thereof, and may be implemented in one or more computer systems or other processing systems. Useful machines for performing some or all of the operations described herein include general-purpose digital computers or similar devices.

Figure 7:
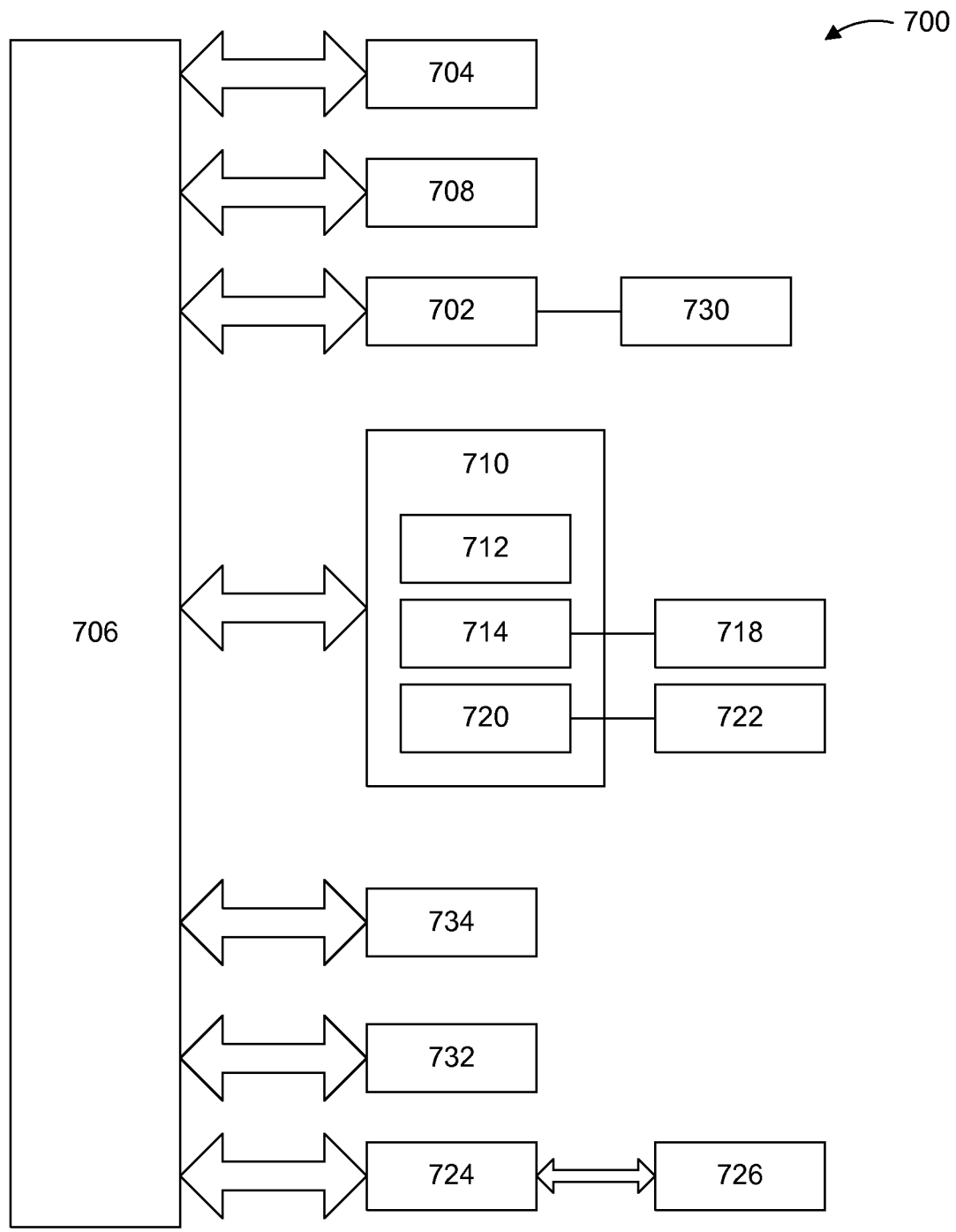
FIG. 7 illustrates a block diagram of a system architecture of a system according to an example embodiment that can perform the processes shown in FIGS. 1A, 1B, and 3 and that can generate data representing the simulated images shown in FIGS. 2 and 4-6.

In fact, one exemplary embodiment employs one or more computer systems equipped to carry out the functions described herein. An example of such a computer system 700 is shown in FIG. 7.

The computer system 700 includes at least one computer processor 704. The processor 704 is connected to a communication infrastructure 706 (e.g., a communications bus, a cross-over bar device, or a network). Although various software embodiments are described herein in terms of this exemplary computer system 700, after reading this description, it will become apparent to a person skilled in the relevant art(s) how to implement the invention using other computer systems and/or architectures.

The computer system 700 also includes a display interface (or other output interface) 702 that forwards video graphics, text, and other data from the communication infrastructure 706 (or from a frame buffer (not shown)) for display on a display unit (or other output unit) 730.

In addition, the computer system 700 includes a main memory 708, which preferably is a random access memory ("RAM"), and also may include a secondary memory 710. The secondary memory 710 can include, for example, a hard disk drive 712 and/or a removable-storage drive 714 (e.g., a floppy disk drive, a magnetic tape drive, an optical disk drive, and the like). The removable-storage drive 714 reads from and/or writes to a removable storage unit 718 in a well-known manner. The removable storage unit 718 may be, for example, a floppy disk, a magnetic tape, an optical disk, and the like, which is written to and read from by the removable-storage drive 714. The removable storage unit 718 can include a computer-usable storage medium having computer software instructions and/or data stored therein.

In alternative embodiments, the secondary memory 710 can include other computer-readable media storing computer-executable programs or other instructions to be loaded into the computer system 700. Such devices can include a removable storage unit 722 and an interface 720 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 722 and interfaces 720 that allow software and data to be transferred from the removable storage unit 722 to the computer system 700.

The computer system 700 also can include a communications interface 724 that enables software and data to be transferred between the computer system 700 and external devices (not shown). Examples of the communications interface 724 can include a modem, a network interface (e.g., an Ethernet card), a communications port (e.g., a Universal Serial Bus ("USB") port or a FireWire® port), a Personal Computer Memory Card International Association ("PCMCIA") interface, and the like. Software and data transferred via the communications interface 724 are in the form of signals, which can be electronic, electromagnetic, optical or another type of signal that is capable of being transmitted and/or received by the communications interface 724. Signals are provided to the communications interface 724 via a communications path 726 (e.g., a channel). The communications path 726 carries signals and can be implemented using wire or cable, fiber optics, a telephone line, a cellular link, a radio-frequency ("RF") link, or the like.

The computer system 700 also can include a digital camera unit 732 that generates data representing images captured by the digital camera unit 732 (see, e.g., Step S104 above). The data generated by the digital camera unit 732 can be processed by the processor 704 and/or stored in the secondary memory 710, for example, and used in one or more of the methods described herein. In addition, the computer system 700 can include a milling unit 734 (which can be computerized or not) that controls a cutting arm to mill a milling block based on received instructions.

As used herein, the phrases "computer program medium" and "computer usable medium" can be used generally to refer to the removable storage unit 718 used with the removable-storage drive 714, a hard disk installed in the hard disk drive 712, for example. These computer program products provide software to the computer system 700. The present invention can be implemented or embodied as one or more of such computer program products.

Computer programs (also referred to as computer control logic) are stored in the main memory 708 and/or the secondary memory 710. The computer programs also can be received via the communications interface 724. Such computer programs include instructions which, when executed by the computer processor 704, enable the computer system 700 to perform the procedures as described herein and shown in, for example, FIGS. 1A, 1B, and 3. Accordingly, such computer programs can control the overall computer system 700.

In an example embodiment described herein implemented using software, the software can be stored in a computer-readable storage medium and loaded into the computer system 700 using the removable-storage drive 714, the hard drive 712, or the communications interface 724. Control logic (software), when executed by the processor 704, causes processor the 704 to perform the procedures described herein.

In an example embodiment described herein implemented primarily using hardware, for example, hardware components such as application-specific integrated circuits ("ASICs"). Implementation of such a hardware arrangement so as to perform the functions described herein will be apparent to persons skilled in the relevant art(s) in view of this description.

Alternatively, example embodiments described herein can be implemented using a combination of both hardware and software.

As will be appreciated by those of skill in the relevant art(s) in view of this description, the example aspects described herein can be implemented using a single computer or using a computer system that includes multiple computers each programmed with control logic to perform various of the above-described functions.

The various embodiments described above have been presented by way of example and not limitation. It will be apparent to persons skilled in the relevant art(s) that various changes in form and detail can be made therein (e.g., different hardware, communications protocols, and the like) without departing from the spirit and scope of the present invention. Thus, the present invention should not be limited by any of the above-described exemplary embodiments, but should be defined only in accordance with the following claims and their equivalents.

The foregoing description has been described in the context of example embodiments in which data representing a candidate prosthetic dental item is analyzed to determine whether a resulting prosthetic item formed using this data will have acceptable aesthetic and structural properties. However, the present disclosure and invention are not limited to that functionality only. Indeed, it also is within the scope of the invention to form the prosthetic dental item directly from a milling block. One skilled in the art will appreciate, in view of the present disclosure, how to adapt the various steps of the method(s) described above, if at all, to design, evaluate, and form prosthetic dental items for animals having teeth.

In addition, it should be understood that the attached drawings, which highlight functionality described herein, are presented as illustrative examples. The architecture of the present invention is sufficiently flexible and configurable, such that it can be utilized (and navigated) in ways other than that shown in the drawings.

Moreover, the example embodiments described herein are not limited to analyzing and/or simulating prosthetic dental items. The example embodiments described herein can be used to analyze and/or simulate virtually any item that can be formed from a block of a material. Moreover, although described herein in the context of an operator performing certain functions of the procedures herein, it should be understood that in other example, the procedures can be performed completely automatically, without operator input.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way.

What is claimed is:

1. A method for evaluating prosthetic dental item data representing a prosthetic dental item, the method comprising:
   acquiring prosthetic dental item data including surface data representing a three-dimensional surface of the prosthetic dental item;
   acquiring milling block data including volume data representing a three-dimensional volume of a corresponding milling block;
   determining whether one or more predetermined characteristics associated with the prosthetic dental item satisfy one or more predetermined acceptability criteria based on the prosthetic dental item data and the milling block data, wherein the one or more predetermined characteristics associated with the prosthetic dental item include a stress distribution of at least one tooth surrounding the prosthetic dental item, wherein the determining includes comparing the stress distribution to a nominal stress distribution, and the determining is performed at least in part by a computer processor; and
   based on a result of the comparing, generating positioning data representing a three-dimensional volume of the prosthetic dental item within the three-dimensional volume of the corresponding milling block.

2. The method of claim 1, further comprising:
   acquiring impression data including surface data representing a three-dimensional surface corresponding to one or more dental surfaces; and
   generating the surface data included in the prosthetic dental item data based on the impression data.

3. The method of claim 1, wherein the predetermined acceptability criteria include a requirement of a physical structure of the prosthetic dental item.

4. The method of claim 1, further comprising performing a structural analysis of the prosthetic dental item based on the prosthetic dental item data and the milling block data, wherein the milling block data includes structural property data representing one or more structural properties of the milling block.

5. The method of claim 1, further comprising outputting the prosthetic dental item data and the milling block data.

6. The method of claim 1, further comprising milling a physical prosthetic dental item based on the prosthetic dental item data and the milling block data.

7. The method of claim 1, further comprising:
   generating aesthetic property data representing one or more aesthetic properties of the prosthetic dental item, based on the prosthetic dental item data, the milling block data, and the positioning data.

8. The method of claim 7, wherein the one or more aesthetic properties include hue, saturation, chrominance, and translucence of at least a portion of the prosthetic dental item.

9. The method of claim 1, wherein the positioning data is generated based on a shape-correlation algorithm or a minimization of shape errors algorithm.

10. The method of claim 1, further comprising calculating a stress distribution of at least one tooth stump to which the prosthetic dental item is to be attached, and the stress distribution of the at least one tooth surrounding the prosthetic dental item.

11. A system for evaluating prosthetic dental item data representing a prosthetic dental item, the system comprising:
    at least one storage unit storing prosthetic dental item data including surface data representing a three-dimensional surface of the prosthetic dental item and milling block data including volume data representing a three-dimensional volume of a milling block; and
    a processor arranged to perform
    (a) determining of whether one or more predetermined characteristics associated with the prosthetic dental item satisfy one or more predetermined acceptability criteria, based on the prosthetic dental item data and the milling block data, wherein the one or more predetermined characteristics associated with the prosthetic dental item include a stress distribution of at least one tooth surrounding the prosthetic dental item, the determining including comparing the stress distribution to a nominal stress distribution, and
    (b) based on a result of the comparing, generating of positioning data representing a three-dimensional volume of the prosthetic dental item within the three-dimensional volume of the corresponding milling block.

12. The system of claim 11,
    wherein the at least one storage unit stores impression data including surface data representing a three-dimensional volume corresponding to one or more dental surfaces, and
    wherein the processor generates the surface data included in the prosthetic dental item data using the impression data.

13. The system of claim 11, wherein the predetermined acceptability criteria include a requirement of a physical structure of the prosthetic dental item.

14. The system of claim 11, wherein the processor performs a structural analysis of the prosthetic dental item based on the prosthetic dental item data and the milling block data, and wherein the milling block data includes structural property data representing one or more structural properties of the milling block.

15. The system of claim 11, wherein the processor outputs the prosthetic dental item data and the milling block data.

16. The system of claim 11, wherein the processor causes a physical prosthetic dental item to be milled based on the prosthetic dental item data and the milling block data.

17. The system of claim 11,
    wherein the processor generates aesthetic property data representing one or more aesthetic properties of the prosthetic dental item, based on the prosthetic dental item data, the milling block data, and the positioning data.

18. The system of claim 17, wherein the one or more aesthetic properties include hue, saturation, chrominance, and translucence of at least a portion of the prosthetic dental item.

19. The system of claim 11, wherein the positioning data is generated based on a shape-correlation algorithm or a minimization of shape errors algorithm.

20. The system of claim 11, wherein the processor further calculates a stress distribution of at least one tooth stump to which the prosthetic dental item is to be attached, and the stress distribution of the at least one tooth surrounding the prosthetic dental item.

21. A method for evaluating prosthetic dental item data representing a prosthetic dental item, the method comprising:
- acquiring prosthetic dental item data including surface data representing a three-dimensional surface of the prosthetic dental item;
- acquiring milling block data including volume data representing a three-dimensional volume of a corresponding milling block;
- determining whether one or more predetermined characteristics associated with the prosthetic dental item satisfy one or more predetermined acceptability criteria based on the prosthetic dental item data and the milling block data, wherein the determining is performed at least in part by a computer processor;
- generating positioning data representing positioning of the volume of the prosthetic dental item within the volume of the milling block; and
- generating aesthetic property data representing one or more aesthetic properties of the prosthetic dental item, based on aesthetic properties of a tooth stump to which the prosthetic dental item is to be attached or aesthetic properties of at least one tooth surrounding the prosthetic dental item, the prosthetic dental item data, the milling block data, and the positioning data.

22. A system for evaluating prosthetic dental item data representing a prosthetic dental item, the system comprising:
- at least one storage unit storing prosthetic dental item data including surface data representing a three-dimensional surface of the prosthetic dental item and milling block data including volume data representing a three-dimensional volume of a milling block; and
- a processor determining whether one or more predetermined characteristics associated with the prosthetic dental item satisfy one or more predetermined acceptability criteria, based on the prosthetic dental item data and the milling block data,
- wherein the processor generates positioning data representing positioning of the volume of the prosthetic dental item within the volume of the milling block, and
- wherein the processor generates aesthetic property data representing one or more aesthetic properties of the prosthetic dental item, based on aesthetic properties of a tooth stump to which the prosthetic dental item is to be attached or aesthetic properties of at least one tooth surrounding the prosthetic dental item, the prosthetic dental item data, the milling block data, and the positioning data.

23. A method for generating positional data in a dental environment, the method comprising:
- acquiring prosthetic dental item data including surface data representing a three-dimensional surface of a prosthetic dental item;
- acquiring milling block data including volume data representing a three-dimensional volume of a corresponding milling block;
- comparing a stress distribution of at least one of a tooth stump to which the prosthetic dental item is to be attached, at least one tooth surrounding the prosthetic dental item, and the prosthetic dental item data, to a nominal stress distribution, the stress distribution being determined based on the data acquired in at least one of the acquirings; and
- based on a result of the comparing, generating positioning data representing a three-dimensional volume of the prosthetic dental item within the three-dimensional volume of the corresponding milling block.

24. A system for generating positional data in a dental environment, the method comprising:
- at least one storage unit storing prosthetic dental item data including surface data representing a three-dimensional surface of a prosthetic dental item, and milling block data including volume data representing a three-dimensional volume of a corresponding milling block; and
- a processor arranged to compare a stress distribution of at least one of a tooth stump to which the prosthetic dental item is to be attached, at least one tooth surrounding the prosthetic dental item, and the prosthetic dental item data, to a nominal stress distribution, the stress distribution being determined based on at least some data stored in the at least one storage unit, the processor also being arranged to generate positioning data representing a three-dimensional volume of the prosthetic dental item within the three-dimensional volume of the corresponding milling block, based on a result of the comparing.

* * * * *